United States Patent [19]

Vora et al.

[11] Patent Number: 5,362,737
[45] Date of Patent: Nov. 8, 1994

[54] METHODS OF TREATING APHTHOUS ULCERS AND OTHER MUCOCUTANEOUS DISORDERS WITH AMLEXANOX

[75] Inventors: Kakubhai R. Vora, Littleton; Atul Khandwala, Aurora, both of Colo.; Charles G. Smith, Sante Fe, Calif.

[73] Assignee: Chemex Pharmaceuticals, Inc., Fort Lee, N.J.

[21] Appl. No.: 6,670

[22] Filed: Jan. 19, 1993

Related U.S. Application Data

[63] Continuation of Ser. No. 682,359, Apr. 9, 1991, abandoned.

[51] Int. Cl.$^5$ .................... A01N 43/40; A61K 31/44; A61K 7/22
[52] U.S. Cl. ........................ 514/291; 424/54; 514/901; 514/902; 514/928
[58] Field of Search .................. 424/49, 54; 514/901, 514/902, 928, 291

[56] References Cited

PUBLICATIONS

Remington's Pharmaceutical Sciences, Mack Publishing Co., 1975, pp. 1438–1439.
Accepted Dental Therapeutics; 38th edition, American Dental Association Chicago, 1979, pp. 257–284.
Handbook of Non prescription Drugs, American Pharmaceutical Association, Washington, D.C., 1977, pp. 249–263.

*Primary Examiner*—Johann Richter
*Assistant Examiner*—Rebecca Cook
*Attorney, Agent, or Firm*—Weiser & Associates

[57] ABSTRACT

A method of treating aphthous ulcers and other mucocutaneous disorders is disclosed. The method comprises contacting the mucocutaneous disorder with a composition in the form of a paste, solution, gel, quick-disintegrating tablet, mouthwash, ointment, cream, powder, adhesive patch, aerosolized spray, lozenge, troche, dentifrice, or dental floss that contains an effective amount of an active compound of the formula:

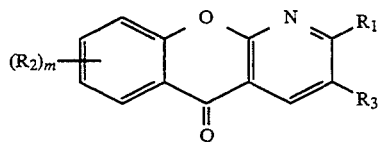

wherein $R_1$ is hydrogen, alkyl, phenyl, carboxyl, hydroxyl, alkoxy, carboxyalkyl (i.e. esters), cyano, acylamino, or amino group which may be unsubstituted or substituted by up to two alkyl groups; m is 0, 1 or 2 and $R_2$ is alkyl, alkenyl, alkoxy, halgoen, nitro, hydroxy, carboxyl, butadienylene ($-CH=CH-CH=CH-$) which forms a benzene ring with any adjacent carbon atoms, cyano, carboxyalkyl, trifluoromethyl, or amino group which may be unsubstituted or substituted by at least one alkyl; and $R_3$ is carboxyl, cyano, arylalkoxycarbonyl, alkoxycarbonyl, or carboxamide which may be unsubstituted or substituted by at least one alkyl, and the salts thereof.

10 Claims, No Drawings

METHODS OF TREATING APHTHOUS ULCERS AND OTHER MUCOCUTANEOUS DISORDERS WITH AMLEXANOX

This application is a continuation of application Ser. No. 07/682,359 filed Apr. 9, 1991 now abandoned.

FIELD OF THE INVENTION

The present invention relates to a method for treating aphthous ulcers and other mucocutaneous disorders.

BACKGROUND OF THE INVENTION

Aphthous ulcers, often referred to as canker sores, are characterized by painful eruptions in the mucous membrane of the mouth. Of unknown etiology, they are covered by a grey exudate, and surrounded by a reddened area. They range in size from several millimeters to two centimeters in diameter. The ulcers are limited to oral mucous membranes not bound to periosteum, e.g. the inner portion of the lip or cheek. Aphthous ulcers may occur as solitary or multiple lesions, and heal spontaneously in one or two weeks. (Steadman's Medical Dictionary, 25th Ed., Williams & Wilkins)

Other mucocutaneous disorders can also result in the formation of oral ulcers that can be extremely painful.

Therapy for mouth ulcers generally involves use of topical anesthetics such as benzocaine in preparations made with a carrier designed to protect the ulcer from saliva and hold the anesthetic at the site. Zilactin is a topical medication composed of hydroxypropylcellulose, salicylic, lauric and tannic acids which has mucosal adherence properties. The mode of action of the product appears to be its effective film-forming capability that insulates the ulcer from the mouth environment. Because this characteristic requires effective formation of such a film, the product is difficult to apply in a manner sufficient to optimize its effect.

Still lacking is a method of treating aphthous ulcers and other mucocutaneous disorders which is easier to apply and which actually speeds the healing of the ulcers. These objectives are achieved by the present invention, which involves the use of oral pastes, troches and mouthwashes which contain as an active ingredient, amelexanox and its analogs.

As disclosed in U.S. Pat. No. 4,143,042, amlexanox is a compound of the formula 2-amino-7-(1-methylethyl)-5-oxo-5H[1]benzopyrano(2,3-b)pyridine-3-carboxylic acid. Amlexanox and its homologs and analogs are known to have anti-allergic activity, and are of value as prophylactic and curative drugs for the treatment of allergic asthma, allergic dermatitis, hay fever and other allergic diseases in mammals, including humans. In Chemical Marketing Reporter, Aug. 14, 1989, it was reported that tests were under way to test use of amlexanox on mouth ulcers. No results were provided.

SUMMARY OF THE INVENTION

It is the principal object of the present invention to provide a novel and effective method of treating aphthous ulcers and other mucocutaneous disorders.

Another object of the present invention is to provide a method of treating aphthous ulcers and the other mucocutaneous disorders in various dosage forms that are convenient to use.

Another object of the invention is to provide a method of treating aphthous ulcers and other mucocutaneous disorders in dosage forms that can be applied at a specific site in the oral cavity with a finger tip or which can be easily masticated for contact with the oral mucosa.

An additional objective of the invention is to provide a method of treating aphthous ulcers and other mucocutaneous disorders in formulations with various release rates for greater efficacy.

To achieve the foregoing objectives and in accordance with the purposes of the invention as embodied and broadly described herein, there is provided a method of treating aphthous ulcers and other mucocutaneous disorders comprising contacting the aphthous ulcer or other mucocutaneous disorder with a composition containing an effective amount of a compound of the formula:

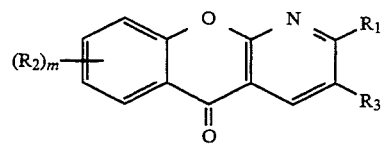

wherein $R_1$ is hydrogen, alkyl, phenyl, carboxyl, hydroxyl, alkoxy, carboxyalkyl (i.e. esters), cyano, acylamino, or amino group which may be unsubstituted or substituted by up to two alkyl groups; m is 0, 1 or 2 and $R_2$ is alkyl, alkenyl, alkoxy, halogen, nitro, hydroxy, carboxyl, butadienylene ($-CH=CH-CH=CH-$) which forms a benzene ring with any adjacent carbon atoms, cyano, carboxyalkyl, trifluoromethyl, or amino group which may be unsubstituted or substituted by at least one alkyl; and $R_3$ is carboxyl, cyano, arylalkoxycarbonyl, alkoxycarbonyl, or carboxamide which may be unsubstituted or substituted by at least one alkyl, and the salts thereof.

DETAILED DESCRIPTION OF THE INVENTION

Amlexanox and its homologs can be used to treat aphthous ulcers and other mucocutaneous disorders. Dosage forms suitable for delivering a drug to the oral mucosal membrane may include paste, solution, gel, quick-disintegrating tablet, mouthwash, ointment, cream, powder, adhesive patch, aerosolized spray, lozenge, troche, dentifrice and dental floss. Although all of these dosage forms are convenient to use, some of them, such as paste, lozenge, troche, solution and gel, may be considered even more advantageous due to the relative ease with which they can be applied at a specific site in the oral cavity with a finger tip, or the ease with which they can be easily masticated for contact with the oral mucosa.

An important physical characteristic for all dosage forms is the rate of release of the drug from the dosage form. It is known, for example, that tablets containing nitroglycerin are formulated to disintegrate quickly under the tongue for immediacy in drug availability to ameliorate anginal pain. This characteristic may not, however, be desirable for all drugs. In drugs which are intended for a topical mode of action, or for a drug which may possess a relatively low rate of absorption through the oral mucosa, it would be desirable to release the drug slowly from the dosage form. Such a slow release rate would minimize swallowing of the drug and would also lower or eliminate the occurrence of pharmacological or toxicological side effects. It is also known that generally a solubilized version of the drug is absorbed faster through the skin and mucous membrane than the solid version. In the case of amlexanox, it was decided to formulate both versions to provide both types of release rates.

Oral paste formulas and troches contain solid crystalline amlexanox. Mouthwash formulas contain the solubilized version of amlexanox.

Oral Paste

The major criteria of a paste for use in the oral cavity are as follows: (1) the paste should adhere to the mucous membrane until the desired amount of drug has been released; (2) the paste should not move from its site of application; (3) it should be composed of safe, edible excipient; (4) it should not alter the taste or should not leave an aftertaste in the mouth; (5) it should be viscous enough to facilitate the application via fingertip, and; (6) it should be homogeneous and non-gritty.

Paste formulas may contain the following categories of ingredients: (1) diluents (also known as fillers) such as dicalcium phosphate, lactose and starch; (2) adhesives that provide adhesion in the presence of saliva and moisture such as gelatin, pectin, acacia gum, xanthan gum and starch derivatives (3) viscosity builders such as microcrystalline wax, carboxymethylcellulose sodium (abbreviated as CMC-Na or CMC Sod or CMC), cross-linked carboxymethylcellulose sodium, petrolatum and polyethylene polymer; (4) plasticizers such as mineral oil and vegetable oils such as olive, safflower, peanut, sesame and sweet almond oil; (5) anionic or nonionic emulsifiers or wetting agents such as glyceryl monostearate, sodium stearate, polysorbate 60, polysorbate 80, Ceteth-20, Steareth-20 and Laureth-23; (6) flavoring agents such as fruit or vegetable flavors, vanilla and chocolate; (7) sweetening agents such as sucrose, saccharin sodium, cyclamate and aspartame; (8) antibacterial preservatives such as benzyl alcohol and sodium benzoate; (9) taste modifiers such as sodium ascorbate, citric acid and sodium tartrate, and; (10) coloring or opaquing agents such as edible colors, dyes and titanium dioxide.

Mouthwash

Amlexanox may be solubilized and formulated into a mouthwash to provide a limited amount of drug in a pleasant-tasting, flavored vehicle which may be used more than once during the day. A distinct advantage of a mouthwash resides in its ability to reach deeper crevices between teeth and the distant areas of the mouth which are inaccessible to the fingertips for a comfortable or convenient mode of application. It is not difficult for a patient to gargle with the medicated mouthwash to provide medication to the deeper areas of the throat.

The following ingredients may be included in a mouthwash formula: (1) diluents such as plain water or flavored water, (2) solvents such as glycerin, ethanol, propylene glycol and other polyols; (3) buffering agents such a sodium citrate and sodium phosphate; (4) organic acids such as citric, phosphoric or tartaric acid; (5) sweeteners such as sucrose, saccharine sodium, cyclamate or aspartame; (6) flavoring agents; (7) coloring agents; (8) preservatives such as sodium benzoate and benzyl alcohol; (9) inorganic acids such as hydrochloric or phosphoric to adjust the pH; (10) water soluble salts such as sodium chloride as taste modifier, and zinc chloride/citrate as astringent, and; (11) antibacterial agents such as cetylpyridinium chloride or benzalkonium chloride at appropriate concentration as allowed by the regulatory authorities.

Troches

Also known as lozenges or pastilles, troches are round discshaped solids containing the drug in a suitable flavored base. The base may be preferably glycerinated gelatin or a mixture of sugar and a mucilagenous gum such as acacia or tragacanth. The drug, i.e., amlexanox or analog may be dispersed at a concentration between 0.1% to 10.0% by weight in a mixture of powdered sugar and powdered acacia or tragacanth. The mucilagenous gum (acacia or tragacanth) may be incorporated in the formula at a concentration of 2% to 10% by weight. The preferred concentration of acacia or tragacanth is between 5% and 8% by weight. This concentration of gum gives sufficient adhesiveness to the mass. The mass is formed by slowly adding water to the mixture of powdered sugar, amlexanox and powdered gum. The water is added until a pliable mass is formed. The mass is rolled out on a clean glass plate and the troche pieces are cut out using a cutter. The mass may be otherwise rolled into a cylinder and divided into pieces of desirable weight. Each piece is then shaped and allowed to dry before packing. Alternate suitable mechanical means may be employed to produce such drug containing troches. The following examples serve to illustrate the method of the invention without restricting said process,

EXAMPLE 1

Table 1 sets forth several paste formulations that were found useful in practicing the method described herein.

TABLE 1

| | FORMULA FOR VEHICLE PASTE | | | | | | | | |
|---|---|---|---|---|---|---|---|---|---|
| | (A) | (B) | (C) | (D) | (E) | (F) | (G) | (H) | (I) |
| Mineral Oil | 27.3 | 26.3 | 38.3 | 36.3 | 46.0 | 28.8 | 28.8 | 47.5 | 32.2 |
| Gelatin | 17.5 | 17.5 | 18.5 | 18.4 | 12.5 | 18.4 | 18.4 | 20.0 | 17.5 |
| Pectin | 17.5 | 17.5 | 18.5 | 18.3 | 12.5 | 18.4 | 18.4 | 20.0 | 17.5 |
| Petrolatum | 11.4 | 11.4 | | 5.0 | | | 3.3 | | |
| Cross-linked Carboxymethylcellulose sodium | | | | 18.3 | 12.5 | | | 10.0 | |
| Carboxymethylcellulose sodium (7HF) | 8.7 | 8.7 | 9.2 | | | 9.2 | 9.2 | | 8.7 |
| Carboxymethylcellulose sodium (7MF) | 8.7 | 8.7 | 9.2 | | | 9.2 | 9.2 | | 8.7 |
| Microcrystalline wax | | | | | | 6.7 | 3.4 | | 12.8 |
| Glyceryl monostearate | 6.4 | 6.4 | | | | 6.7 | 6.7 | | |
| Polyethylene | | | 4.3 | 3.6 | 4.0 | | | 2.5 | |
| Xanthan gum | | | | | 12.5 | | | | |
| Titanium dioxide | | 1.0 | 2.0 | | | | | | 1.1 |
| Benzyl alcohol | 2.5 | 2.5 | | | | 2.6 | 2.6 | | 1.5 |
| Flavor, Sweetner | qs | qs | qs | qs | qs | | | | |

EXAMPLE 2

The following ranges of excipients (percent weight/weight) were found useful in vehicle pastes.

| Excipient | Percent w/w Range |
|---|---|
| Mineral Oil | 27.0–47.5 |
| Gelatin | 12.0–20.0 |
| Pectin | 12.0–20.0 |
| Petrolatum | 3.0–11.5 |
| Cross-linked CMC Sodium | 10.0–20.0 |
| CMC Sodium (7HF) | 8.0–10.0 |
| CMC Sodium (7MF) | 8.0–10.0 |
| Microcrystalline wax | 3.0–7.0 |
| Glyceryl monostearate | 3.0–10.0 |
| Polyethylene | 2.0–4.5 |
| Xanthan gum | 1.0–15.0 |
| Titanium dioxide | 0.1–3.0 |
| Benzyl alcohol | 0.5–3.0 |

Final Composition of Paste

| Ingredient | PERCENT WEIGHT/WEIGHT | | | | |
|---|---|---|---|---|---|
| AMLEXANOX | 10.0 | 7.5 | 5.0 | 2.5 | 0.1 |
| VEHICLE | 90.0 | 92.5 | 95.0 | 97.5 | 99.9 |

Method of Preparation of Oral Paste

Screen all the solids through a suitable sieve such as 60 or 70 mesh sieve and then mix the preweighed amounts in a suitable blender such as a V-Blender until adequately mixed. In a separate suitable vessel add weighed formula amounts of mineral oil, petrolatum, surfactant such as glyceryl monostearate, polysorbates and polyethylene. Heat this vessel with constant stirring until a homogeneous fluid is obtained. While slowly cooling with continuous stirring add the blended solids and keep stirring to obtain a homogeneous dispersion of solids in the oil phase. At 45°–50° C. add the preservatives and cool down to room temperature with continuous stirring. Pass the final semisolid product through an ointment roller mill to homogenize the product.

EXAMPLE 3

The formulas described below represent particularly preferred mouthwash formulations:

| Ingredient | Percent weight/weight | | |
|---|---|---|---|
| Water | 81.7 | 82.3 | 83.2 |
| Ethanol | 12.8 | 12.8 | 12.8 |
| Glycerin | 3.0 | 3.0 | 3.0 |
| Sodium citrate | 0.2 | — | — |
| Citric acid | 0.2 | — | — |
| Triethanolamine | 1.0 | 0.7 | 0.7 |
| Amlexanox | 1.0 | 1.0 | 1.0 |
| Flavoring agent | 0.1 | 0.1 | 0.1 |
| Coloring agent | q.s. | q.s. | q.s. |
| Hydrochloric acid | — | q.s. to pH 7.5 | q.s. to pH 7.5 |

The above mentioned ingredients may be used in the percent (w/w, range described below to obtain a more suitable version:

| Ingredient | Percent w/w range |
|---|---|
| Water | 60.0–95.0 |
| Ethanol | 8.0–15.0 |
| Glycerin | 1.5–6.5 |
| Sodium citrate | 0.1–0.9 |
| Citric acid | 0.1–1.0 |
| Triethanolamine | 0.1–1.5 |
| Amlexanox | 0.1–1.5 |
| Flavoring agent | 0.1–1.0 |
| Coloring agent | 0.1–1.0 |
| Astringent Salt | 0.1–1.5 |

Method of Preparation Of Mouthwashes

To a suitable vessel add the formula amount of amlexanox and add designated amount of triethanolamine. Stir to mix well. To this mixture, add while stirring, ethanol, glycerin, water, buffering agents, flavors and colors. Stir well to mix.

EXAMPLE 4

The following amlexanox pastes formulations were tested and found useful in the treatment of aphthous ulcers:

| Formula No. 04-27a(A) | |
|---|---|
| AC-9 Homopolymer(polyethylene; Allied) | 3.8% |
| Kaydol Mineral Oil (viscosity 340–355) | 38.3% |
| Pectin, USP | 17.4% |
| Gelatin, NF | 18.1% |
| CMC-Na 7MF (Aqualon) | 8.7% |
| CMC-Na 7HF (Aqualon) | 8.7% |
| Amlexanox | 5.0% |
| Formula No.: 04-27a(C) | |
| AC-9 Homopolymer(polyethylene; Allied) | 4.3% |
| Kaydol Mineral Oil (viscosity 340–355) | 38.5% |
| Pectin, USP | 17.4% |
| Gelatin, NF | 17.4% |
| CMC-Na 7MF (Aqualon) | 8.7% |
| CMC-Na 7HF (Aqualon) | 8.7% |
| Amlexanox | 5.0% |

Paste Manufacturing Procedure

1) Screen gelatin to a fine mesh (preferably 100 mesh sieve).
2) Mechanically grind pectin to a fine powder.
3) To a blender add pectin, gelatin, CMC 7HF and CMC 7MF
4) To a separate container add AC-9 homopolymer and mineral oil and heat to 90 C or until mixture is clear and homogeneous.
5) While hot, add step 3 to step 4 with stirring and cool to room temperature with constant stirring.
6) Mill the mixture from step 5 on a 3-roll mill until homogeneous This formulation appears to be physically stable after aging 2 weeks at 40° C.

EXAMPLE 5

Study Summary

Objective

The objective of this clinical study was to evaluate the tolerance and efficacy of 5% amlexanox adhesive paste when applied to patients with aphthous ulcers.

Study Plan

This 4-day clinical study utilized a double-blind, randomized, uneven parallel-group, multi-center design.

Thirty-five patients with aphthous ulcers who met all of the inclusion and none of the exclusion criteria were enrolled into this study. Patients were treated on the buccal mucosa, oral labial mucosa, floor of mouth or the distal half of the tongue.

Patients enrolled into the study were treated with either the 5% amlexanox adhesive paste or the vehicle adhesive paste. The study drug was applied to a maximum of 3 ulcers identified for treatment twice daily for 3 days. Tolerance and efficacy evaluations were made twice daily and again in the morning of the fourth day.

RESULTS

Demographic and Background Data

Data consisted of information from 35 patients who were treated with either the 5% amlexanox (aml.) adhesive paste or the vehicle.

| | Demographics | | |
|---|---|---|---|
| Study Drug | Total Patients Enrolled | No. Safety Analysis | No. Efficacy Analysis |
| 5% aml. | 21 | 21 | 18 |
| Vehicle | 14 | 14 | 14 |
| Total | 35 | 35 | 32 |

Efficacy

The efficacy data was generated from an evaluation of the signs and symptoms of the patients with the aphthous ulcers. The evaluations included a measurement of ulcer size, the severity of erythma and pain, and an evaluation of overall improvement. The evaluations were made twice daily for three days and again on the morning of the fourth day. The following table summarizes the results from all study sites.

| Summary of Efficacy Evaluations | | | | | |
|---|---|---|---|---|---|
| | Median | | Mean | | |
| Evaluation | 5% aml. | Vehicle | 5% aml. | Vehicle | p. value |
| % Reduction in Pain | 93% | 57% | 73% | 61% | |
| % Reduction in Size | 88% | 37.5% | 69% | 41% | |
| Erythema* | −4 | 1−.5 | −2.9 | −1.4 | |
| Improvement | 3 | 0.5 | 2.4 | 0.9 | <0.0001 |

*ERYTHEMA ADJUSTMENT SCALE

−4 = No Erythema     0 = No Change from Day 1 AM
−3 = Marked Decrease     1 = Slight Increase
−2 = Moderate Decrease     2 = Moderate Increase
−1 = Slight Decrease     3 = Marked Increase

PHYSICIAN'S IMPROVEMENT SCALE

| Grade | Description of Ulcer |
|---|---|
| 4 | = Aphthous ulcer cleared |
| 3 | = Marked improvement (the ulcer is barely perceptible with minimal or no pain and marked decrease in size) |
| 2 | = Moderate improvement (the ulcer is visible with moderate decrease in erythema and a moderate decrease in pain and moderate decrease in size) |
| 1 | = Slight improvement (the ulcer is visible with a slight decrease in size, minimal decrease in erythema and a slight decrease in pain) |
| 0 | = No change from the A.M. Day 1 |
| −1 | = Aphthous ulcer worsened (greater erythema and/or pain or size) |

Safety

The safety of the 5% amlexanox oral paste was assessed on the basis of the incidence, nature and severity of the adverse experiences reported during the study. During the conduct of this study no adverse experiences were reported.

Discontinuations

A total of 3 patients discontinued therapy with the 5% amlexanox oral paste. All three patients discontinued due to conflicts in scheduling.

Conclusion

Patients with aphthous ulcers who had been treated twice-a-day for three days with 5% amlexanox showed clinically significant improvement in all parameters measured over the vehicle paste. Statistical significance was seen in the measurements of ulcer size, reduction in erythema and overall improvement. No adverse reactions of any type were reported by either the patient or the investigator during the study.

What is claimed is:

1. A method for speeding the healing of aphthous ulcers as determined by the reduction of the size of the ulcers which method consists essentially of reducing the size of the ulcers by administering topically to the oral mucosal membrane a composition which comprises a compound of the formula: 2-amino-7-(1-methylethyl)-5-oxo-5H-[1]benzopyrano(2,3-b) pyridine-3-carboxylic acid or a pharmaceutically acceptable salt thereof in an effective concentration and a pharmaceutically acceptable vehicle.

2. The method of claim 1 wherein the concentration of the compound in the composition is from about 1 to about 5%.

3. The method of claim 2 wherein the concentration of the compound in the composition is about 1%.

4. The method of claim 2 wherein the concentration of the compound in the composition is about 5%.

5. The method of claim 1 wherein the compound is administered for three days.

6. The method of claim 1 wherein the vehicle is selected from the group consisting of an oral paste, a masticatable gum, a solution, a gel, a disintegrating tablet, a mouthwash, an ointment, a cream, a powder, an aerosolized spray, a lozenge, a troche, a dentifrice and dental floss.

7. The method of claim 1 wherein the composition is administered on the buccal mucosa, oral labial mucosa, floor of the mouth or distal half of the tongue.

8. The method of claim 1 wherein the reduction of ulcers' size is statistically significant.

9. The method of claim 1 wherein the reduction of ulcers' size is a clinically significant improvement.

10. The method of claim 1 wherein the speeding of healing as determined by reduction of the ulcers' size is observable separately from reduction of erythema.

* * * * *